United States Patent [19]

Buschur

[11] Patent Number: 5,668,478
[45] Date of Patent: Sep. 16, 1997

[54] WINDSHIELD RAIN SENSOR

[75] Inventor: Jeffrey J. Buschur, Bellbrook, Ohio

[73] Assignee: ITT Automotive Electrical Systems, Inc., Auburn Hills, Mich.

[21] Appl. No.: 440,910

[22] Filed: May 15, 1995

[51] Int. Cl.$^6$ .................. G01R 27/26; H01G 7/00
[52] U.S. Cl. .................. 324/690; 324/660; 324/664; 324/686; 318/483; 361/284
[58] Field of Search ............ 73/335.02, 335.03, 73/335.04, 335.05; 324/690, 660, 664, 686, 694, 696, 724; 361/281, 284, 286; 318/443, 444, 483

[56] References Cited

U.S. PATENT DOCUMENTS

| | | | |
|---|---|---|---|
| 3,826,979 | 7/1974 | Steinmann | 324/664 |
| 4,127,763 | 11/1978 | Roselli | 318/483 |
| 4,492,904 | 1/1985 | Graham | 318/444 |
| 4,527,106 | 7/1985 | Fischer | 318/483 |
| 4,639,831 | 1/1987 | Iyoda | 361/286 |
| 4,665,351 | 5/1987 | Nyberg | 318/483 |
| 4,703,237 | 10/1987 | Hochstein | 318/483 |
| 4,705,998 | 11/1987 | Millerd et al. | 318/444 |
| 4,710,878 | 12/1987 | Iyoda | 364/424 |
| 4,797,605 | 1/1989 | Palanisamy | 324/65 R |
| 4,805,070 | 2/1989 | Koontz et al. | 361/286 |
| 4,827,198 | 5/1989 | Uueller et al. | 318/444 |
| 4,831,493 | 5/1989 | Wilson et al. | 361/286 |
| 4,897,585 | 1/1990 | Millerd et al. | 318/483 |
| 4,942,349 | 7/1990 | Millerd et al. | 318/483 |
| 4,960,996 | 10/1990 | Hochstein | 250/349 |
| 5,040,411 | 8/1991 | Medzius | 73/73 |
| 5,057,754 | 10/1991 | Bell | 318/483 |
| 5,119,002 | 6/1992 | Kato et al. | 318/444 |
| 5,140,234 | 8/1992 | Wallrafen | 318/264 |
| 5,157,314 | 10/1992 | Kuhbauch | 318/443 |
| 5,210,500 | 5/1993 | Pingel et al. | 324/667 |
| 5,262,640 | 11/1993 | Purvis et al. | 250/227.25 |
| 5,296,819 | 3/1994 | Kuroiwa et al. | 73/335.04 |
| 5,304,936 | 4/1994 | Buschur | 324/689 |
| 5,336,980 | 8/1994 | Levers | 318/444 |
| 5,402,075 | 3/1995 | Lu et al. | 73/335.04 |
| 5,453,676 | 9/1995 | Agrotis et al. | 318/444 |
| 5,598,146 | 1/1997 | Schroder | 318/444 X |

Primary Examiner—Glenn W. Brown
Attorney, Agent, or Firm—Thomas N. Twomey; J. Gordon Lewis

[57] ABSTRACT

The invention concerns rainwater sensors for windshields. In one embodiment, a first, inner, conductive film is applied to the inner surface of the windshield, and a second film, of same size and shape as the first, is applied to the outer surface. However, a narrow strip is removed from the second film, forming a gap which divides the second film into parts 1 and 2. The resulting structure forms two capacitors, namely: (1) inner film plus part 1, and (2) inner film plus part 2. The impedance of one capacitor is monitored. When rain occurs, it falls into the gap between parts 1 and 2, and acts as a resistor, bridging part 1 to part 2. This bridging adds a new impedance in parallel with the first capacitor, thereby changing the effective impedance. This change indicates the presence of rain.

4 Claims, 9 Drawing Sheets

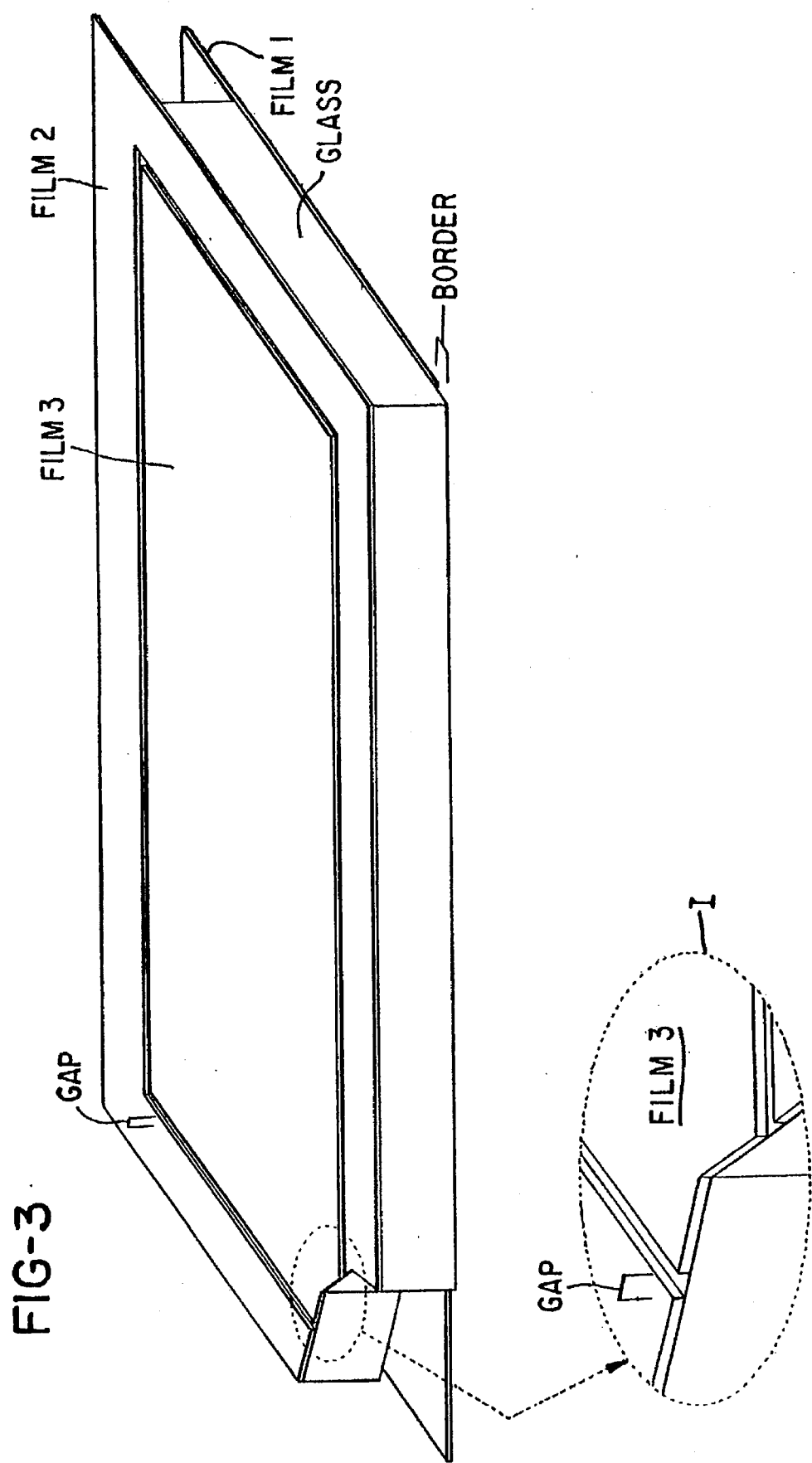

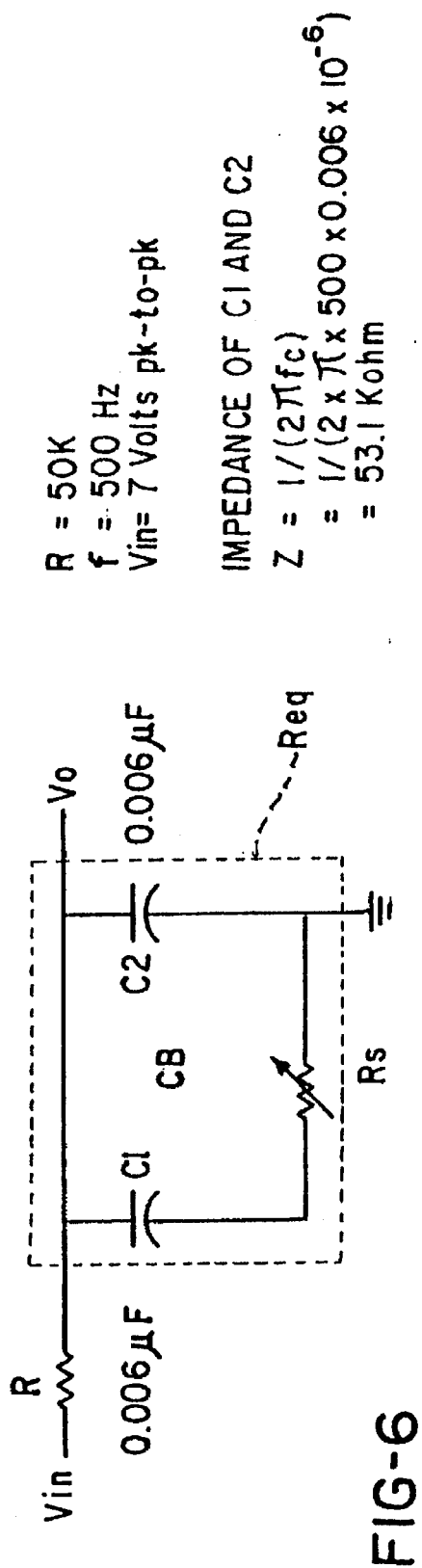
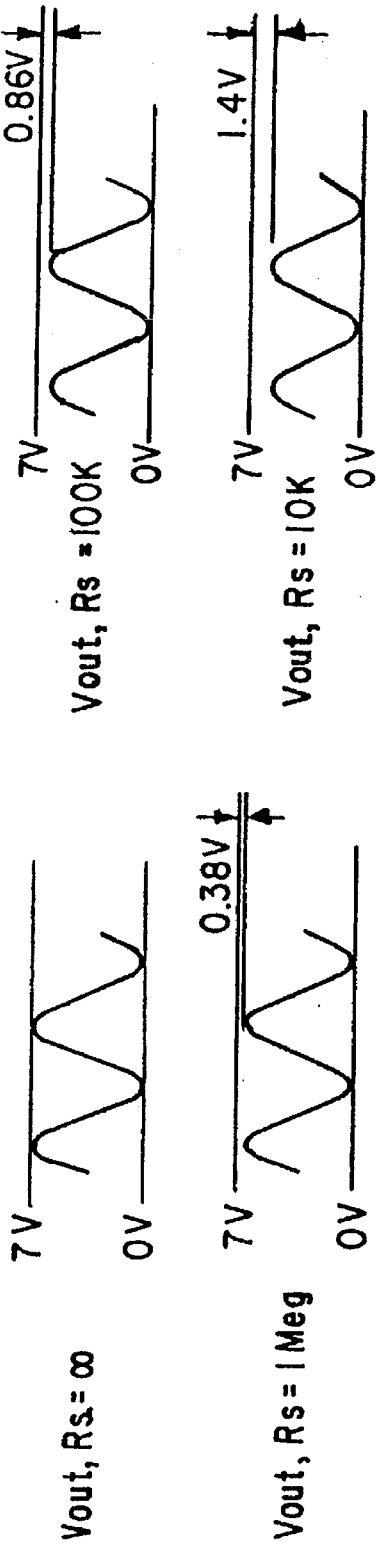
FIG-6

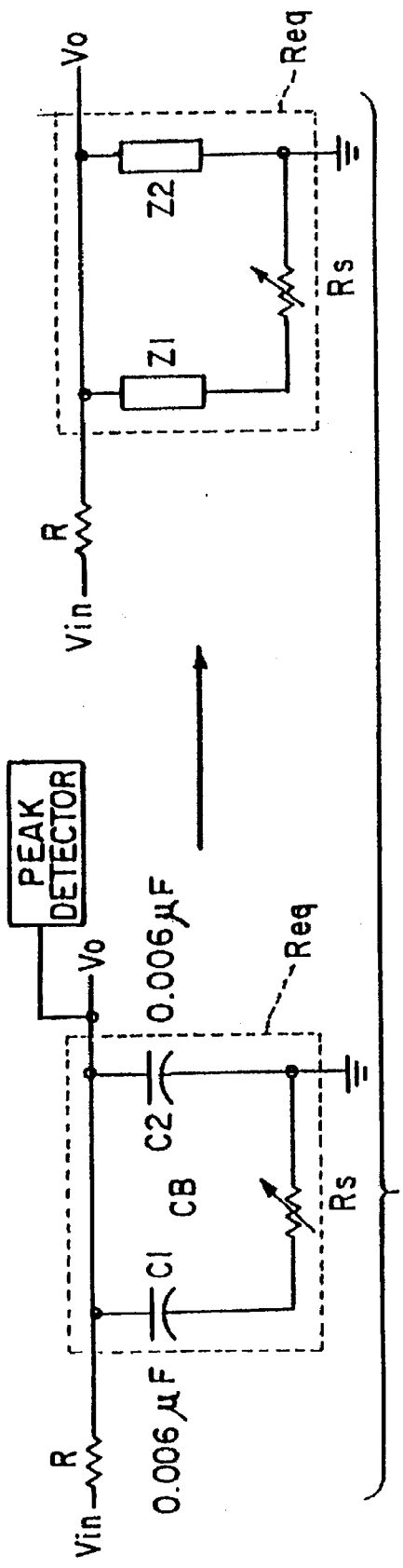
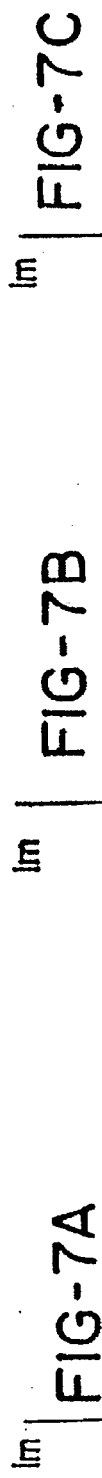
FIG-7A FIG-7B FIG-7C FIG-7D

WINDSHIELD RAIN SENSOR

The invention concerns a sensing system for detecting rainwater on an automobile windshield, in order to actuate windshield wipers.

BACKGROUND OF THE INVENTION

When an automobile driver travels long distances through rain, the driver must continually adjust the speed of the windshield wipers, because the intensity of the rain striking the windshield continually varies. Variation is caused by the natural variation in rain over time and distance, and also by man-made agents, such as passing vehicles, which shower nearby automobiles with spray.

This continual adjustment can be tedious, and rain sensors have been developed, in order to automate control of the wipers. FIG. 1 is a schematic view of a WINDSHIELD, and illustrates one type of sensor. The swaths S represent the fields swept by the wiper blades.

The sensor takes the form of parallel conductors C. When water bridges the gap G between the conductors, the electrical resistance of the gap G changes. A resistance sensor (not shown) detects this change, infers the presence of water, and calls for a wiping stroke.

This type of sensor presents some disadvantages. One is cost of manufacture. The long, finger-like conductors C are fabricated in a sequence of multiple steps which include masking, screening, and firing processes. The multiplicity of steps imposes cost.

Also, the conductor sections which are located outside the swaths S, such as at region R, must be protected from the rainwater, because the wipers do not remove the water in this region. Consequently, insulation is added to the conductors in this region, to insulate them from the water. Without insulation, the sensors would continually detect rain, and continually call for wiping strokes.

One solution to this particular problem is capacitive coupling, as described in U.S. Pat. No. 4,827,198. However, such coupling is not feasible in some windshields which bear a metallic film on the interior surface. Such films are used as resistance heaters, in order to de-frost the windshield.

OBJECTS OF THE INVENTION

An object of the invention is to provide an improved rain sensor for automobile windshields.

Another object of the invention is to provide a rain sensor which is compatible with metallic heating films, or IR-reflective films, carried by an automobile windshield.

SUMMARY OF THE INVENTION

In one form of the invention, conductive films on a windshield act as first and second capacitors, which are ordinarily disconnected from each other. Impedance of the first capacitor is monitored. When rain occurs, rainwater connects an added impedance (which includes the second capacitor) in parallel with the first capacitor, thereby changing the measured impedance of the first capacitor. The change in impedance indicates the presence of rain.

BRIEF DESCRIPTION OF THE DRAWINGS

FIG. 3 shows the subject matter of FIG. 2 in greater detail, with sections removed.

FIG. 6 illustrates how Vo changes as Rs changes. Rs is the resistance created by the rainwater.

FIGS. 7A, 7B, and 7C illustrate three phasor diagrams which justify the transformation of FIG. 7D.

FIG. 7D illustrates a transformation of the complex impedances of the equivalent circuit of FIG. 5 into purely real impedances.

DETAILED DESCRIPTION OF THE INVENTION

Film Structure

Figure 1:
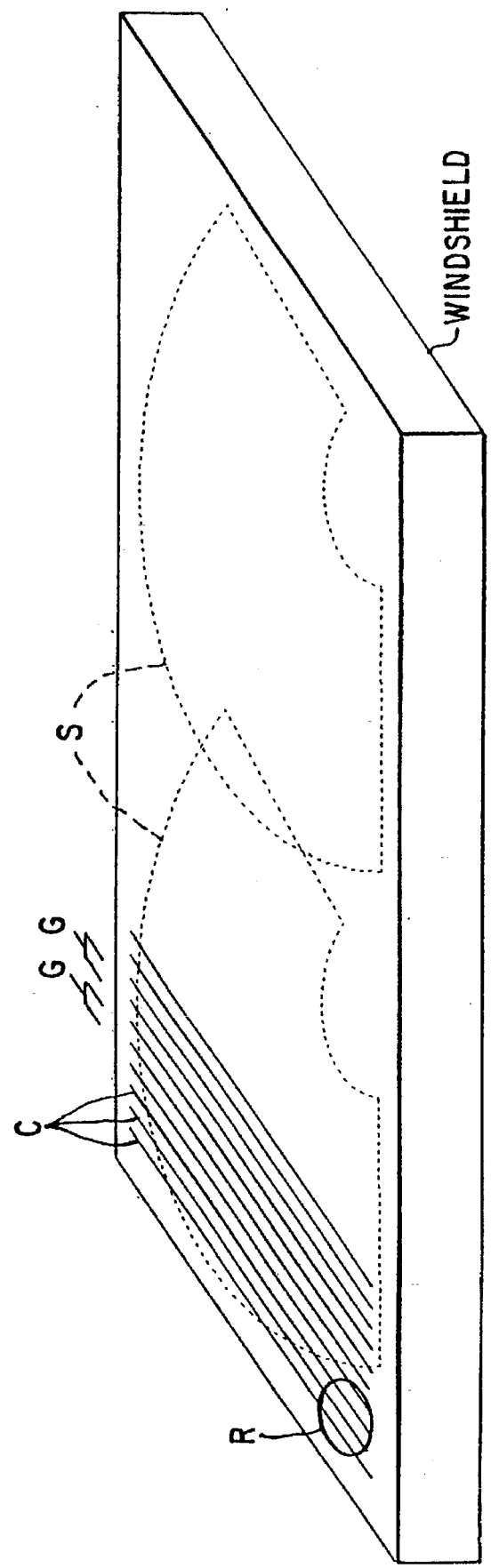
FIG. 1 is a schematic illustration of an automobile windshield.
Figure 2:
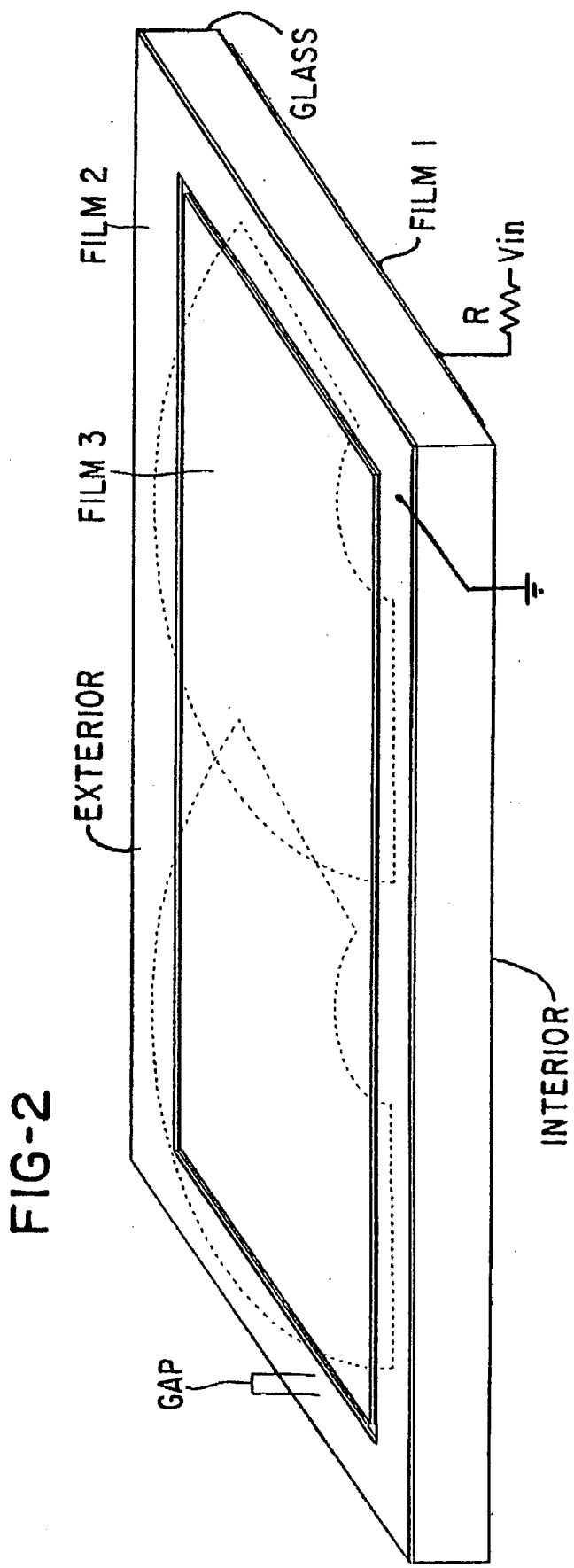
FIG. 2 illustrates one form of the invention.
Figure 2A:
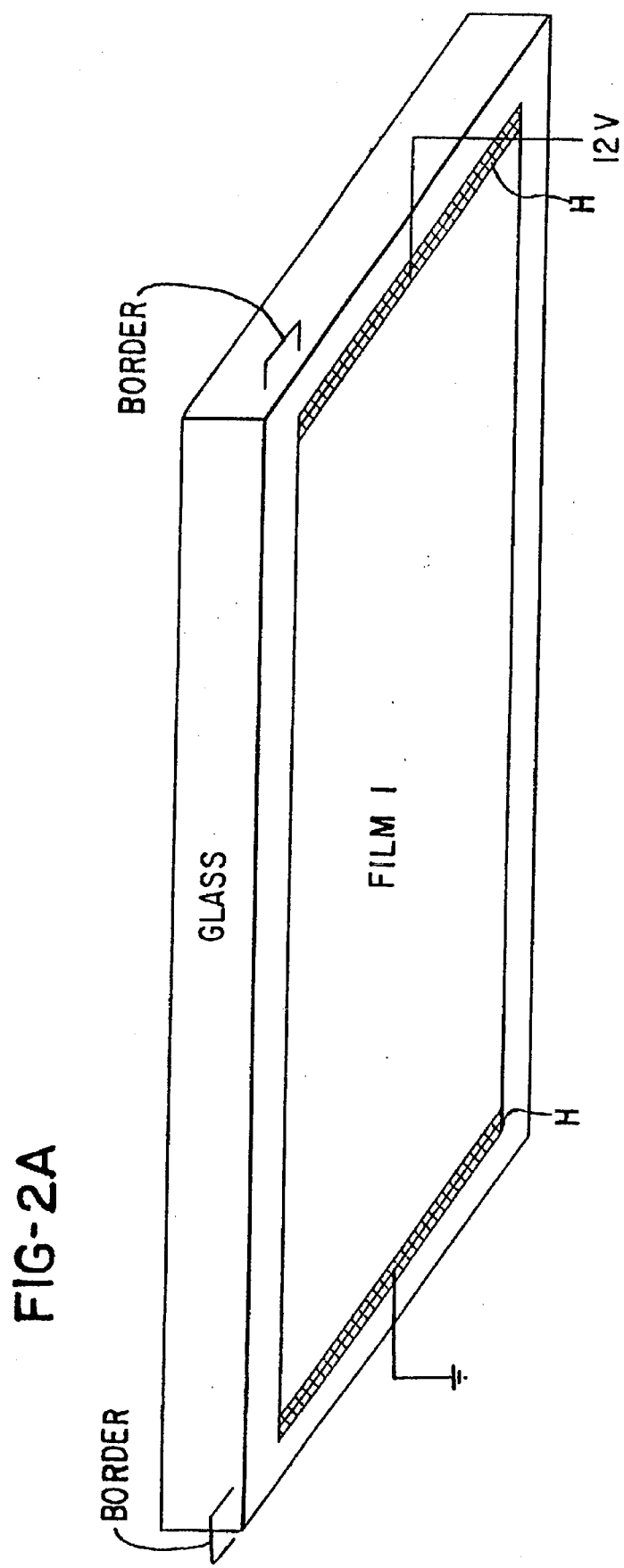
FIG. 2A illustrates the interior surface of the windshield of FIG. 2.

FIGS. 2, 2A, and 3 illustrate the physical structure of one form of the invention. The interior surface of the GLASS of the windshield is coated with a conductive FILM 1, indicated in FIG. 2. FILM 1 may be eliminated along the periphery labeled BORDER, as shown in FIG. 2A, to assist processing and isolation.

FILM 1 can be the type used in windshield resistance heating. FIG. 2A shows a 12-volt source and a ground connection, which deliver power to FILM 1. Hatched regions H indicate conductors which distribute current to FILM 1. The thickness of FILM 1 will vary, depending on the metal used, but, in general, lies in the range of a few hundred Angstroms. This thickness is sufficient to provide a continuous, conductive coating of metal, but sufficiently thin to be nearly transparent.

The exterior surface, which is cleaned by the wipers, is coated with a similar film, but this film is divided into two parts by a GAP, as indicated in FIG. 3. That is, FILM 2 is electrically insulated from FILM 3 by the GAP (in the absence of rainwater). An insert I shows the GAP in enlarged format.

Figure 4:
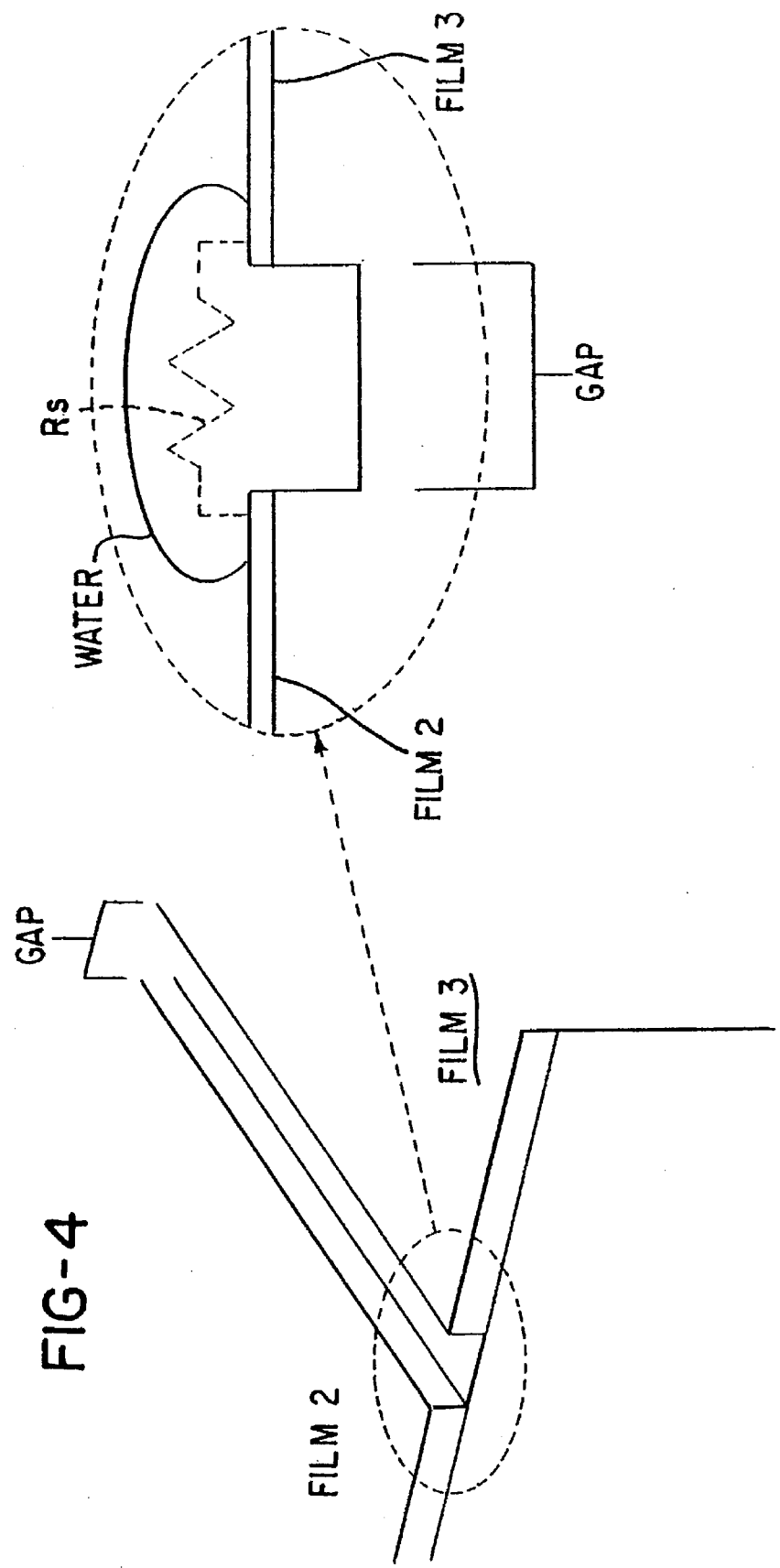
FIG. 4 illustrates how rainwater bridges the GAP and forms a resistor connecting FILM 2 and FILM 3.

When rainwater falls onto the GAP, as indicated in FIG. 4, it acts as a resistor Rs which bridges FILM 2 and FILM 3. When this bridging resistance Rs is detected, rainwater is inferred to be present.

Detection

Figure 5:
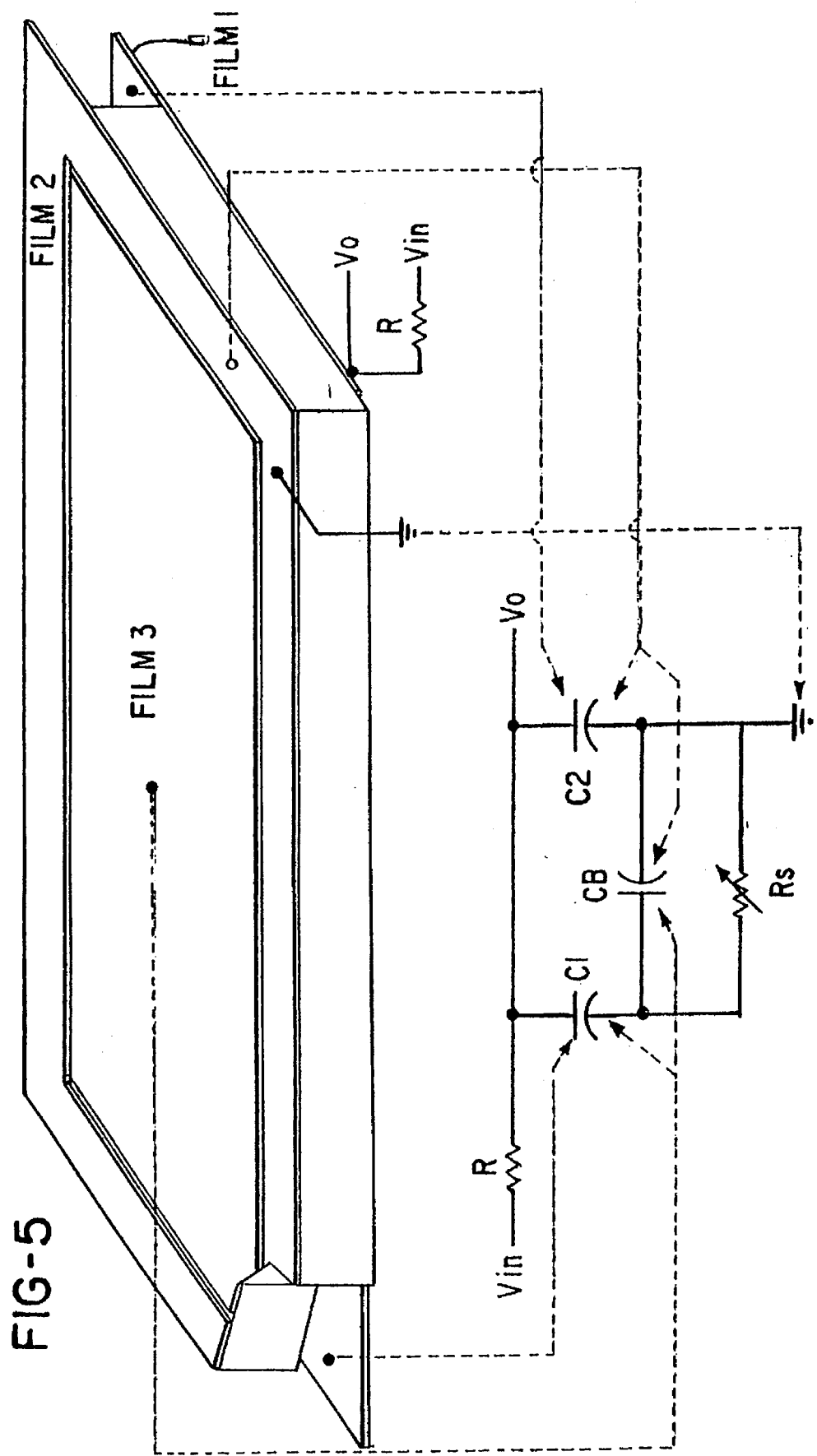
FIG. 5 illustrates the equivalent electrical circuit which the structure of FIG. 2 creates.

FIG. 5 illustrates the structure of FIG. 3, but with additional components, including:

1) the ground symbol connected to FILM 2,
2) the lead labeled Vo, connected to FILM 1, and
3) the resistor R, also connected to FILM 1, and connecting to a signal source Vin.

FIG. 5 also illustrates an equivalent circuit which describes the electrical behavior of the structure. The FILMs act as plates of capacitors, as indicated by the arrows. For example, capacitor C2 is composed of FILM 1 and FILM 2. Rainwater generates the variable resistor Rs.

Value of Total Capacitance

An estimate of the values of the capacitances can be made as follows. One type of windshield has a surface area of 1,300,000 square mm, and a thickness of 2.3 mm. (Thickness refers to the thickness of the GLASS in FIG. 3.) If it is assumed that the relative dielectric constant of the GLASS is 5.0, then the total capacitance of the structure shown in FIG. 5 is 0.025 microFarads. If it is assumed that FILM 2 and FILM 3 contain equal surface areas, then capacitances C1 and C2 are approximately equal, at about 0.012 microFarad each.

Capacitor CB

Capacitor CB represents the capacitance between the two FILMs located on the outer surface, namely, FILM 2 and FILM 3. (The material within the GAP acts as the dielectric.) This capacitance is extremely small, in the range of 200 picoFarads, and can be ignored, for present purposes. That is, 200 picoFarads corresponds to $200 \times 10^{-12}$ Farads, while the value of C1 and C2 are each about $120 \times 10^{-10}$ Farad, about 100 times larger.

Detection Process

Req, in the upper left part of FIG. 6, together with R, act as a voltage divider. Req acts as one leg of the divider, and R acts as the other. The fraction of Vin which reaches Vo depends on Req, which depends on Rs.

Thus, when raindrops create the WATER shown in FIG. 4, Rs changes, thereby changing Vo. The change in Vo indicates the presence of rain. Further, as rain intensity increases, causing more water to fill the GAP shown in FIG. 3, the extra water further reduces Rs, by, in effect, placing more resistances in parallel. How changes in Req causes changes in Vo will now be explained.

Simplification

The computation of Vo can be simplified by treating the impedances of capacitances C1 and C2 as being real (as opposed to imaginary). If these impedances are treated as real, then the voltage division ratio can be computed as a series-parallel combination of real components. This computation is much simpler than a series-parallel combination of complex impedances, which requires complex algebra, having real and imaginary parts.

FIG. 7, top, shows a transformation of capacitors C1 and C2 into real impedances. This transformation can be justified on the following grounds.

At a given frequency, the impedances Z1 and Z2 remain constant. The total impedance of Z1 in series with Rs is the vector sum of $-jZ1$ plus Rs, as indicated in FIG. 7A. However, there are three possible cases.

If Rs is small, Compared with Z1, as in FIG. 7A, then the vector sum is approximately equal to Z1.

If Rs is large, compared to Z1, as in FIG. 7B, then the vector sum is approximately equal to Rs.

If Rs is equal to Z1, as in FIG. 7C, then the vector sum equals (square root of 2)×Rs. If the vector sum is simplified to the algebraic sum, the error in the simplification is about 50 percent, but only occurs when Rs equals Z1. For example, if Rs and Z1 both equal unity, their vector sum is 1.4 in magnitude, but their algebraic sum is 2.0. The error is about 50 percent. This error is sufficiently small for present purposes, which is to illustrate the trend of how Vo changes as Rs changes.

With this simplification, at a frequency of 500 Hz, Z1 and Z2 are computed to be 53.1 Kohms (real), as indicated in the upper right part of FIG. 6. Req is now given by the following expression:

$$Req = [(53.1\ K + Rs) \times 53.1\ K]/[53.1\ K + Rs + 53.1\ K]$$

This expression indicates that Req depends on Rs. As Rs changes, Vo changes. Some examples will illustrate.

Exemplary Plots

The table located in FIG. 6, right center, illustrates Req computed for four different values of Rs. The four plots located at the bottom of FIG. 7 illustrate how Vo, labeled "Vout," changes with these four values of Rs. (Vin is a constant frequency signal at 500 Hz, 7.0 volts peak-to-peak.) A peak detector, shown at the upper left of FIG. 7, can be used to detect when the voltage drops to a selected level, and trigger the windshield wipers.

Alternate Embodiments

FILM Covers only Driver's Side

Figures 8, 9:
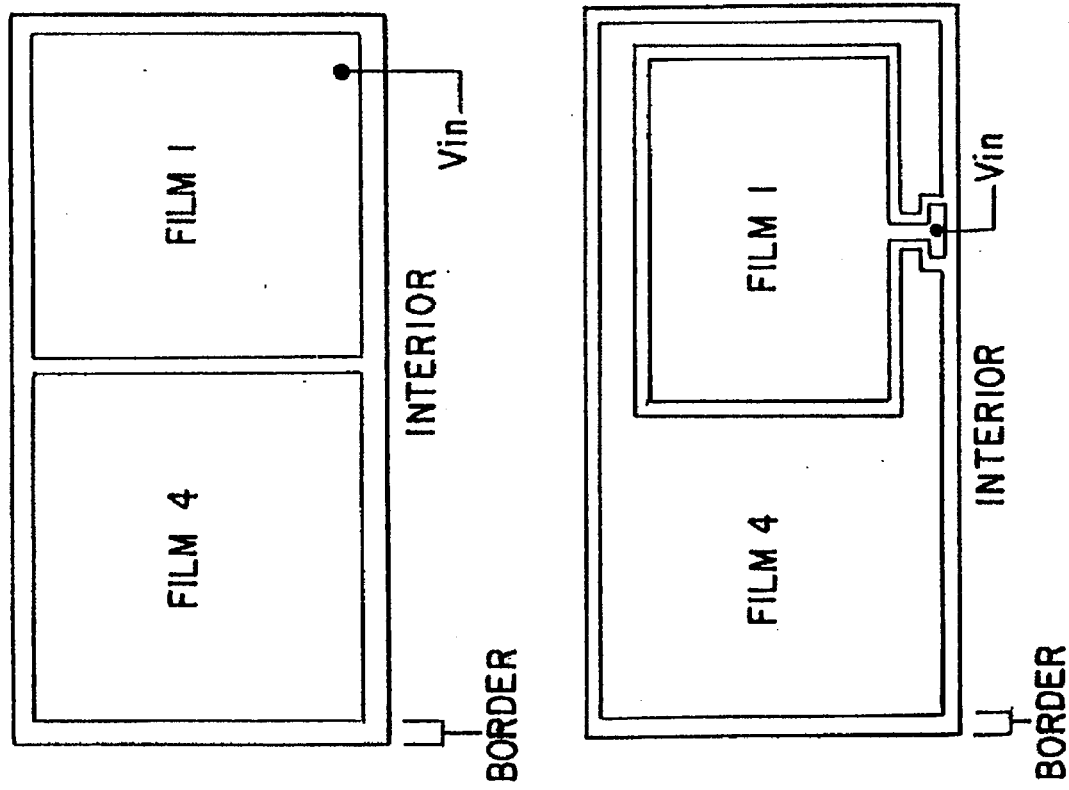
FIGS. 8 and 9 illustrate alternate embodiments of the invention.

FIG. 8 illustrates an embodiment wherein FILM 3 covers only the driver's part of the windshield, thereby eliminating the passage of the GAP across the passenger's viewing area of the windshield. The film on the interior surface of the windshield has been divided into two parts. With this division, provision must be made to supply current to both parts for heating.

Increased Sensitivity to Changes in Rs

FIG. 9 illustrates an embodiment wherein the capacitive coupling from FILM 1 to FILM 2 is significantly reduced, because of reduced overlap, thereby reducing the value of capacitor 2 in FIG. 5. With this reduction, the sensitivity of the equivalent circuit in FIG. 5 to changes in Rs is significantly increased. However, use of FILM 1 and FILM 4 as heat sources may be difficult.

Additional Considerations

1. It is not necessary to use the simplified computation given above. An exact computation of the voltage division ratio, using complex quantities, is straightforward, though perhaps tedious.

2. One view of the invention is that it includes capacitor C2 in FIG. 7, which is ordinarily not connected to C1, because, in the absence of rain, Rs is not present (or, equivalently, has an extremely high value). The impedance seen by the input resistor R is that of C2 alone. C2, plus R, form the voltage divider.

However, when rain generates Rs, the impedance seen by R drops, because a complex impedance (comprising C1 and Rs) is now placed in parallel with C2. The voltage division fraction changes.

3. Addition of the series combination of Rs-plus-Z1 in parallel with Z2 in FIG. 7 reduces the effective impedance of Z2. The voltage divider principle allows one approach to detecting this change. Other approaches are possible. For example, the change causes a change in the RC time constant of the former Z2. The new RC constant can be detected, as known in the art.

4. The voltage divider can be said to possess a "division fraction." In the case of the voltage divider of FIG. 7, the division fraction is Req/[R+Req].

5. One or more of the films can be constructed to block infra-red radiation, in order to reduce "greenhouse effect" heating of the automobile.

6. As shown in FIGS. 2, 8, and 9, film 3 is completely contained within the wiped area.

7. Windshields are commonly constructed of two layers, or lamina, of glass. These lamina are bonded to a transparent sheet of plastic sandwiched between them, in order to provide resistance to shattering in the event of impact.

These two lamina provide four surfaces to which the films can be applied: the inner lamina contains an inner surface 10 and an outer surface 13, and the outer lamina contains an inner surface 16 and an outer surface 19. FIG. 2 shows application of the films to (i) the outer surface of the outer lamina, and (ii) the inner surface of the outer lamina. Other combinations of the surfaces can be chosen.

In particular, application of film to the surface adjacent the transparent plastic film can be advantageous, because those surfaces are protected from damage by external agents.

Numerous substitutions and modifications can be undertaken without departing from the true spirit and scope of the invention. What is desired to be secured by Letters Patent is the invention as defined in the following claims.

I claim:

1. A rain sensor assembly for an automobile windshield having an exterior surface, comprising:
    a) a first conductive film located on the exterior surface, and divided into a first exterior film part and a second exterior film part by a gap;
    b) a second conductive film spaced apart from the first conductive film, wherein (1) said first exterior film part and said second conductive film form a first capacitor, and (2) said second exterior film part and said second conductive film form a second capacitor;
    c) a circuit for detecting (1) a first impedance across the first capacitor when no rainwater is present in the gap, and (2) a second impedance across the first capacitor when rainwater is present in the gap, wherein said circuit includes said first capacitor and said second capacitor in parallel with each other when rainwater is present in the gap.

2. A rain sensor assembly according to claim 1 in which the gap presents a resistance between the first exterior film part and the second exterior film part which is
    i) high in the absence of rainwater; and
    ii) low in the presence of rainwater.

3. A rain sensor assembly according to claim 1, wherein said circuit further includes:
    a ground connected to the first exterior film part;
    a resistor, having
        i) one terminal connected to the second conductive film; and
        ii) another terminal connected to a voltage source running at fixed frequency; and
    an output terminal connected to the second conductive film.

4. A rain sensor for a windshield having interior and exterior surfaces, comprising:
    a) a first conductive film located on the interior surface;
    b) means for delivering current to the first conductive film, for heating said film;
    c) a second conductive film located on the exterior surface, which is divided into two parts by a gap which presents a resistance which is
        i) high in the absence of rainwater; and
        ii) low in the presence of rainwater;
    d) means for presenting a time-varying signal to the first conductive film, through a resistor; and
    e) means for detecting a change in voltage of the first conductive film when said resistance changes.

* * * * *

UNITED STATES PATENT AND TRADEMARK OFFICE
CERTIFICATE OF CORRECTION

PATENT NO. : 5,668,478
DATED : September 16, 1997
INVENTOR(S) : Buschur et al.

It is certified that error appears in the above-identified patent and that said Letters Patent is hereby corrected as shown below:

In column 3, line 8, please delete "microFarad" and insert --microFarads-- therefor.

In column 3, line 17, please delete "Farad" and insert --Farads-- therefor.

In column 6, line 24, claim 4, please delete "," and insert --and-- therefor.

Signed and Sealed this

Tenth Day of February, 1998

Attest:

BRUCE LEHMAN

Attesting Officer

Commissioner of Patents and Trademarks